United States Patent [19]
Wu

[11] Patent Number: 5,298,783
[45] Date of Patent: Mar. 29, 1994

[54] COMBINED SEMICONDUCTOR GAS SENSOR

[75] Inventor: Xinghui Wu, Kunming, China
[73] Assignee: Yunnan University, China
[21] Appl. No.: 903,781
[22] Filed: Jun. 24, 1992
[30] Foreign Application Priority Data
Sep. 9, 1991 [CN] China ............... 91108927.6
[51] Int. Cl.$^5$ ............................. H01L 29/66
[52] U.S. Cl. ........................ 257/414; 338/34; 73/30.04; 204/415; 204/416; 204/418; 204/419
[58] Field of Search ............ 257/414, 410, 411; 204/415, 416, 418, 419; 73/30.01, 30.02, 30.03, 30.04; 338/34

[56] References Cited

U.S. PATENT DOCUMENTS

| | | | |
|---|---|---|---|
| 4,305,724 | 12/1981 | Micko | 23/232 E |
| 4,413,502 | 11/1983 | Ohta et al. | 73/23 |
| 4,568,445 | 2/1986 | Cates et al. | 204/419 X |
| 4,929,313 | 5/1990 | Wrighton | 204/415 X |
| 5,078,855 | 1/1992 | Mochizuki et al. | 257/414 X |
| 5,145,645 | 9/1982 | Zakin et al. | 338/34 X |

FOREIGN PATENT DOCUMENTS

2-226061  9/1990  Japan .................. 73/30.01

Primary Examiner—William Mintel
Attorney, Agent, or Firm—Skjverve, Morrill, MacPherson, Franklin & Friel

[57] ABSTRACT

The present invention relates to a combined semiconductor gas sensor, this sensor is constituted by combining two portions, each of the portions is made of a different gas sensitive material, their resistance exhibit different variation with the variation of the density of a specific gas, a detecting signal is led out from the junction of the two portion. Because of the mutual compensation and propagation effect of the two portions of the above mentioned gas sensor, the stability and/or sensitivity as well as the stability to temperature and humidity and the initial relaxation time can be improved. Gas sensors of different characteristics can be obtained by different combinations of two different gas sensitive materials selected according to need.

24 Claims, 4 Drawing Sheets substrate

COMBINED SEMICONDUCTOR GAS SENSOR

BACKGROUND OF THE INVENTION

The present invention relates to a semiconductor gas sensor, and particularly to a combined semiconductor gas sensor constituted by two different gas sensitive materials, which has high sensitivity and preferable selectivity, thermo-stability and anti-humidity capability.

Recently, semiconductor gas sensors have become one of the most rapidly developed and widely used gas sensors for their advantages of relatively high sensitivity, uncomplicated manufacturing techniques, convenient and flexible usage, etc. More and more types of semiconductor gas sensors have also been developed, the kinds of gases that can be detected have been increasing rapidly, from the detection of flammable and explosive gas to the detection of poisonous gases, fragrance, stink, as well as freshness. Some of the gases used in producing of semiconductors and integrated circuits are of severe poison, the density to be detected is in the range of 1-100 ppm, and sometimes even in the magnitude of ppb's. In view of poisoning preventing and personal safety, it is also required to be extended to the detection of low density ones in many occasions. For example, for preventing slow poisoning, the allowable average density of $H_2S$ for eight-hour working is 15 ppm, and 150 ppm for CO; for preventing acute poisoning, the allowable density for fifteen-minute exposure to $H_2S$ is 100 ppm, and to CO is 400 ppm. The existing gas sensors can hardly satisfy this measuring requirement.

As for methods for improving the sensitivity of semiconductor gas sensors, the recently adopted methods include:
1. adding catalyst to improve the activity of gas sensitive materials;
2. super-parculate of the material;
3. searching for new materials with desirable sensitivity.

However, the improvement of sensitivity of gas sensors by the use of such methods is of certain limitation, detections of ppb level can hardly be realized by the sensors manufactured by these methods.

Furthermore, the existing gas sensors are of simple structures constituted by doping a gas sensitive substrate material with characteristic-improving dopant, the selecting characteristic of which is not good enough and the stability is poor. In order to improve the stability in application, a thermosensitive resistor is usually connected externally for compensation, and sometimes, the gas sensitive detecting head is combined with the temperature compensating element. Since the above-mentioned temperature compensating element is a thermosensitive resistor, it can only be used for temperature compensating but not for humidity compensating, without any contribution to the improvement of the selectivity of the gas sensor, and any improving effect to the sensitivity and initial relaxation time of the sensor.

SUMMARY OF THE INVENTION

The present invention provides a combined semiconductor gas sensor constituted by combining two portions, these two portions are made of different semiconductor gas sensitive materials of different gas sensitive characteristics or/and electrical conduction types respectively, the resistances of which vary differently with the variation of density of certain gas. When this combined gas sensor is connected into a detecting circuit, a signal is led out from the junction of the two materials, one of the above-mentioned two portions is used as the load simultaneously. Two gas sensitive materials are selected according to need, and combined to form an integral gas sensor which may have higher sensitivity and/or selectivity, as well as better stability to temperature and humidity, and may improve the initial relaxation time.

Therefore, it is one of the objects of the present invention to provide a combined gas sensor having better selectivity.

It is another object of the present invention to provide a combined gas sensor having high sensitivity.

It is yet another object of the present invention to provide a gas sensor having both high sensitivity and good selectivity.

It is another object of the present invention to provide a gas sensor having improved thermo-stability, humidity stability and initial relaxation time together with improved selectivity and/or sensitivity.

DETAILED DESCRIPTION OF THE INVENTION

The combined gas sensor of the present invention consists of two portions made of two different gas sensitive materials respectively, the constitution of which can be of the four different types of N-N, P-P, N-P, P-N, the characteristics of the integral gas sensor can be changed by different selections of the two materials. Selectivity can be improved by using the N-N-type or P-P-type, while sensitivity, or both sensitivity and selectivity can be improved by using the N-P-type or P-N-type. And all of the integral gas sensors constituted by those combinations are of desirable thermo-stability, anti-humidity capability, as well as good response and recovery time.

Discussion on the selectivity of the element

Figures 1, 2, 3:
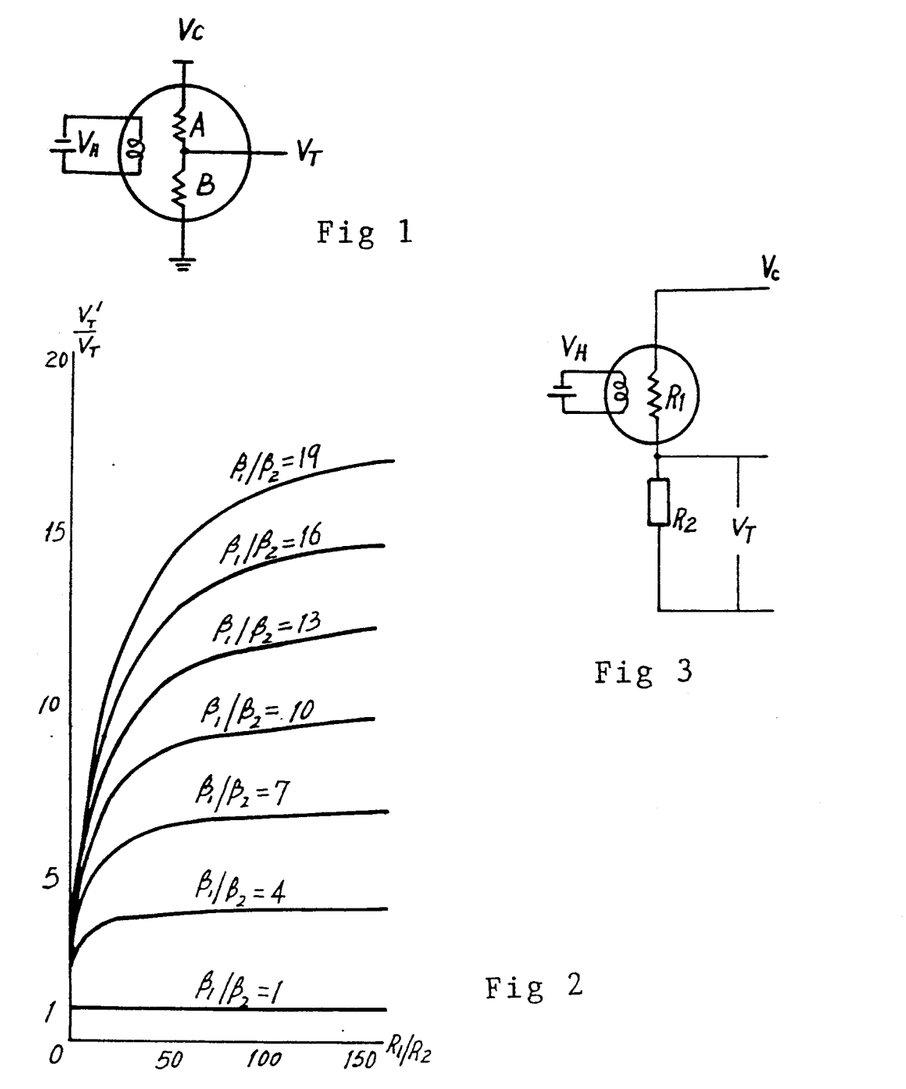
FIG. 1 is a schematic diagram showing the operating principle of the combined gas sensor according to the present invention.
FIG. 2 shows the curves of the selectivity analysis of the element according to the present invention.
FIG. 3 is a schematic diagram showing the operating principle of common gas sensor.
Figure 4:
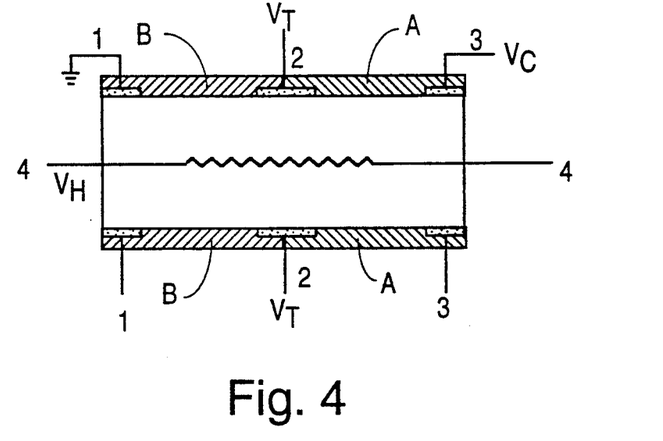
FIG. 4 shows a sectional view of the sintered gas sensor according to the present invention.

In order to obtain a gas sensor having good selectivity, a gas sensitive material A sensitive to the gas to be detected but insensitive to interference gas(es) and another gas sensitive material B sensitive to interference gas(es) but insensitive to the gas to be detected can be selected and combined together to constitute an integral gas sensor, the signal detected is led out from the junction of A and B, wherein B operates as load simultaneously, as shown in FIG. 1. Both materials A and B can be N-type or P-type semiconductor material, therefore, the integral gas sensor constituted can be of the type of N-N or P-P. As for the problem of how N-P type and P-N type realize selectivity, it will be discussed in "Discussion on sensitivity".

As shown in FIG. 1, it is a schematic diagram showing the operating principle of the gas sensor of the present invention. In FIG. 1, $V_H$ indicates the heating voltage, $V_C$ indicates the working voltage, while $V_T$ indicates the output voltage, where A and B represent the two portions constituted by two gas sensitive materials A and B respectively.

Taking the N-N-type as example now, provided that the resistance of portion A in clean air is $R_A$ and that of portion B is $R_B$, and their resistances after contacting with a certain gas are $R_A'$ and $R_B'$ respectively, then the sensitivities of materials A and B to this gas are respectively:

$$\beta_A = \frac{R_A}{R_A'}, \text{ and } \beta_B = \frac{R_B}{R_B'}$$

the output voltage in clean air is $V_T$, which becomes $V_{T'}$ after contacting with the gas, then $$\frac{V_{T'}}{V_T} = \left(\frac{R_B'}{R_A' + R_B'}\right) \bigg/ \left(\frac{R_B}{R_A + R_B}\right)$$

$$= \left(1 + \frac{R_B}{R_A}\right) \bigg/ \left(\frac{\beta_B}{\beta_A} + \frac{R_B}{R_A}\right)$$

The family of curves shown in FIG. 2 can be obtained from the above equation, it can be seen that:
(1) where $\beta_A > \beta_B$, $V_{T'} > V_T$ and output voltage increases;
(2) where $\beta_A = \beta_B$, $V_{T'} = V_T$ and output voltage remains unchanged;
(3) where $\beta_A < \beta_B$, $V_{T'} < V_T$ and output voltage decreases.

It can be seen from the above that if material A is selected with a sensitivity to the gas to be detected greater than that of material B, that is, in conformity with the first condition, then a output voltage increases, and at the same time the sensitivity of material A to the interference gas(es) is less than that of material B, that is, in conformity with the third condition, where the output voltage decreases, thereby, distinguishing between the gas to be detected and the interference gas(es) can be preferably realized, thus the selectivity of the element can be improved.

Generally speaking, the resistance of N-type semiconductor decreases while contacting reduction gases and increases while contacting with oxidation gases, while the resistance of P-type semiconductors is quite the contrary. According to this characteristic, the N-N-type or P-P-type structure can be used for manufacturing gas sensors with selectivity for reduction gases, and the N-P-type or P-N-type structure can be used for manufacturing general purposed or wide-scope gas sensors, and gas sensors with selectivity of different gases can be obtained by different combinations of the two materials.

Discussion on the sensitivity of the element

To improve the sensitivity of the element, two semiconductor materials A and B of different types of conductivity but both sensitive to the gas to be detected are employed by the present invention to constitute the two portions respectively, these two portions are combined together to constitute an integral gas sensor, and its operating principle is shown in FIG. 1. Materials A and B can be N-type and P-type respectively, or P-type and N-type respectively, the element formed can be of N-P-type and P-N-type. Because, when contacting the gas to be detected, the resistance of N-type material decreases as the density of the gas increases, while the resistance of P-type material increases as the density of the gas increases, then the circuit is connected as shown in FIG. 1, the value of the partial voltage $V_T$ of the two portions constituted by these two materials used as the voltage of the output signal, increases a lot compared to that of the output signal of the gas sensor constituted by only one gas sensitive material as shown in FIG. 3, thereby, the sensitivity is significantly improved. The detailed analysis is as follows:

Provided that the resistances in clean air of the gas sensitive materials A and B constituting the two portions of the combined gas sensor are $R_A$ and $R_B$ respectively, and the corresponding output signal voltage is $V_T$, after contacting the gas to be detected, the resistances of the two portions A and B become $R_A'$ and $R_B'$ respectively, and correspondingly the output signal voltage becomes $V_{T'}$, then the sensitivity of the integral combined element is defined as:

$$\beta = \frac{V_{T'}}{V_T} \tag{1}$$

Taking materials A and B respectively N-type and P-type semiconductor gas sensitive materials as example, the corresponding sensitivities are defined respectively as:

$$\beta_A = R_A/R_A' \tag{2}$$

$$\beta_B = R_B'/R_B \tag{3}$$

Because the resistance of N-type semiconductor gas sensitive material decreases as the density of gas increases, while the resistance of P-type semiconductor material increases as the density of gas increases, thus, we have $\beta_A > 1$ and $\beta_B > 1$.

From FIG. 1:

$$V_T = \frac{R_B}{R_A + R_B} V_C \tag{4}$$

$$V_{T'} = \frac{R_B'}{R_A' + R_B'} V_C \tag{5}$$

Substituting (4) and (5) into (1), and using (2) and (3), we have $$\beta = \frac{1 + R_B/R_A}{1 + R_B'/R_A'} \beta_A \beta_B \tag{6}$$

The following is a discussion on various possible conditions of equation (6).
1. In condition $R_A >> R_B$
   (i) where $R_A' >> R_B'$
   $\beta = \beta_A \beta_B$, noticing that we have $\beta_A > 1$ and $\beta_B > 1$ for A being N-type and B being P-type material, therefore $\beta > \beta_A$ or $\beta_B$.
   (ii) where $R_A' = R_B'$ $$\beta = \beta_A \beta_B \frac{R_A'}{R_A' + R_B'} = \frac{1}{2} \beta_A \beta_B$$

(iii) where $R_A' < R_B'$ $$\beta = \beta_A \beta_B \left(\frac{R_A'}{R_A' + R_B'}\right)$$

2. In condition $R_A = R_B$
   (i) where $R_A' > R_B'$ $$\beta = \beta_A \beta_B \left( \frac{2}{1 + R_B'/R_A'} \right) < 2\beta_A\beta_B, \text{ but } \beta > \beta_A\beta_B$$

(ii) where $R_A' = R_B'$ $$\beta = \beta_A \beta_B$$

(iii) where $R_A' < R_B'$ $$\beta = \beta_A \beta_B \left( \frac{2}{1 + R_B'/R_A'} \right) < \beta_A\beta_B$$

3. In condition $R_A < R_B$
  (i) where $R_A' > R_B'$ $$\beta = \beta_A \beta_B \left( \frac{1 + R_B/R_A}{1 + R_B'/R_A'} \right) > \beta_A\beta_B$$

(ii) where $R_A' = R_B'$ $$\beta = \beta_A \beta_B \left( \frac{1 + R_B/R_A}{2} \right) > \beta_A\beta_B$$

(iii) where $R_A' < R_B'$ $$\beta = \beta_A \beta_B \left( \frac{1 + R_B/R_A}{1 + R_B'/R_A'} \right) \begin{cases} > \beta_A\beta_B, \text{ for } \left( \frac{R_B}{R_A} > \frac{R_B'}{R_A'} \right) \\ = \beta_A\beta_B, \text{ for } \left( \frac{R_B}{R_A} = \frac{R_B'}{R_A'} \right) \\ < \beta_A\beta_B, \text{ for } \left( \frac{R_B}{R_A} < \frac{R_B'}{R_A'} \right) \end{cases}$$

It can be seen from the above discussion that except for the conditions 1 (ii), 1(iii), 2(iii) and part of the conditions in 3 (iii), the sensitivity $\beta$ of the element in all other conditions can be made greater than or equal to $\beta_A\beta_B$. In fact, for convenience in use, normally, the element is designed to satisfy the condition of 1 (i) for the structure of this element, that is, it is only needed to make the resistances of materials A and B in clean air satisfy $R_A >> R_B$, and where the density of the gas to be detected is not very high, satisfy $R_A' >> R_B'$(or $R_A' > R_B'$), thereby, the sensitivity of the integral combined gas sensor can be made higher than that of the common gas sensor.

Furthermore, it should be pointed out that at the same time of improving the sensitivity of the element, the selectivity of the element will be improved as well, the analysis is as follows:

Supposing that the sensitivity of material A to the gas (I) to be detected be $\beta_{AI}$, and the sensitivity to the interference gas (II) be $\beta_{AII}$, then the resolution of material A to these two gases is defined as:

$$\alpha_A = \frac{\beta_{AI}}{\beta_{AII}}$$

Similarly, the resolution of material B to these two gases is defined as:

$$\alpha_B = \frac{\beta_{BI}}{\beta_{BII}}$$

And the resolution of the integral gas sensor to these two gases is defined as:

$$\alpha = \frac{\beta_I}{\beta_{II}}$$

$\beta_{BI}$ and $\beta_{BII}$ are the sensitivities of material B to gases (I) and (II) respectively, and $\beta_I$ and $\beta_{II}$ are the sensitivities of the integral gas sensor to gases (I) and (II) respectively.

Where the sensitivity of the integral gas sensor satisfies $\beta = \beta_A\beta_B$, then its resolution is:

$$\alpha = \frac{\beta_I}{\beta_{II}} = \frac{\beta_{AI}\beta_{BI}}{\beta_{AII}\beta_{BII}} = \alpha_A\alpha_B$$

It can be learnt from the above equation that where both gas sensitive materials A and B constituting the integral gas sensor are of certain selectivity to the gas (I) to be detected, i.e., $\beta_{AI} > \beta_{AII}$ and $\beta_{BI} > \beta_{BII}$, then $\alpha > \alpha_A$ or $\alpha_B$, that is, the resolution of the integral gas sensor is greater than that of single gas sensitive material. This reveals that the combined structure can also improve the selectivity of the gas sensor.

It can be learnt from the above discussion that where $R_A > R_B$ and $R_A' >> R_B'$(or $R_A' > R_B'$), the condition $\beta = \beta_A\beta_B$ can be satisfied, that is, where $R_A >> R_B$ and $R_A' >> R_B'$(or $R_A' > R_B'$), the sensitivity of the element can be improved. In the meantime, if both gas sensitive materials A and B are of selectivity to the same gas, then not only sensitivity but also selectivity can be improved by the combined gas sensor. Of course, the above discussion is directed to N-P-type element, i.e., in the combined gas sensor, the portion working as the load simultaneously is of the P-type material and the other portion is of N-type material.

Discussion on the thermo-stability of the element

Firstly, the thermo-stability of gas sensors with common structure (i.e., constituted by one gas sensitive material) is discussed.

Referring to FIG. 3, it is a schematic operating diagram of a gas sensor with common structure, the temperature coefficient of the gas sensor is:

$$\gamma_1(T) = \frac{1}{R}\frac{dR}{dT},$$

where the change of temperature is not very large, it can be approximated by $$\gamma_1 = \gamma_1(T) = \frac{1}{R}\frac{\Delta R}{\Delta T}$$

When the temperature changes from $T_1$ to $T_2 = T_1 + \Delta T$ the resistance of the gas sensor changes from $R_1$ to $R_1 + R_1\gamma_1\Delta T$, and the resistor R2, which serves simultaneously as load in FIG. 3, is a fixed resistor which does not change with temperature. Provided that the output voltages at temperatures $T_1$ and $T_2$ are $V_{T1}'$ and $V_{T2}'$ respectively then $$V_{T1}' = \frac{R_2}{R_1 + R_2} V_C = \frac{V_C}{1 + R_1/R_2} \quad (7)$$

$$V_{T2}' = \frac{R_2 V_C}{R_2 + R_1 + R_1 \gamma_1 \Delta T} = \frac{V_C}{1 + (1 + \gamma_1 \Delta T) R_1/R_2} \quad (8)$$

Comparing equation (7) with equation (8), in order to make the output voltage invariable with temperature, $(1+\gamma_1\Delta T)$ should be made approaching 1, i.e., $\Delta T \rightarrow 0$ or $\gamma_1 \rightarrow 0$, however, the conditions are difficult to satisfy, and normally $R_1$ is much greater than $R_2$ $(1+\gamma_1\Delta T)R_1/R_2$ will vary greatly when $1+\gamma_1\Delta T$ deviating from 1 slightly, thereby causing relatively large fluctuations in the output voltage $V_T$.

The following is a discussion of the thermo-stability of the combined gas sensor of the present invention.

As for the combined gas sensor of the present invention, it is different from the above mentioned situations. As shown in FIG. 1, the resistance $R_B$ of the thermo-sensitive material portion serving as load simultaneously is not fixed, it can be selected to have the same variation tendency of resistance with temperature as that of $R_A$. If the materials are selected appropriately, it is possible to make the partial voltage of the two portions A and B, i.e. the output signal voltage, not vary with temperature or exhibit very small variation. Some detailed analyses will be discussed in the following.

Referring to FIG. 1, supposing that when temperature changes from $T_1$ to $T_2$, the output signal voltage of the element changes from $V_{T1}$ to $V_{T2}$, and the resistance of gas sensitive material portion A changes from $R_A$ to $R_A + R_A\gamma_A\Delta T$, and that of gas sensitive material portion B changes from $R_B$ to $R_B + R_B\gamma_B\Delta T$, then output signals $V_{T1}$ and $V_{T2}$ are $$V_{T1} = \frac{R_B}{R_A + R_B} V_C = \frac{V_C}{1 + R_A/R_B} \quad (9)$$

$$V_{T2} = \frac{R_B + R_B \gamma_B \Delta T}{(R_A + R_A \gamma_A \Delta T) + (R_B + R_B \gamma_B \Delta T)} \quad (10)$$

$$V_C = \frac{V_C}{1 + \frac{R_A}{R_B}\left(\frac{1 + \gamma_A \Delta T}{1 + \gamma_B \Delta T}\right)}$$

respectively. Comparing equation (9) with equation (10), in order to make $V_{T2}$ approach $V_{T1}$, then $$\frac{1 + \gamma_A \Delta T}{1 + \gamma_B \Delta T} \rightarrow 1 \quad (11)$$

is required. In order to establish equation (11), there could be two conditions:

(i) $1+\gamma_A\Delta T = 1+\gamma_B\Delta T$, i.e., $\gamma_A = \gamma_B$.

This indicates that when the temperature coefficients of the two gas sensitive materials are equal, the output signal will not vary with temperature. Of course, it is difficult to strictly satisfy $\gamma_A = \gamma_B$, because even if the materials used are fully identical, there may still be slight difference due to different manufacturing processes and unequal thickness of coatings of materials, etc. However, where $\gamma_A$ and $\gamma_B$ are selected to be equal or approximately equal, the thermo-stability of the combined gas sensor will be desirable.

(ii) $\gamma_A\Delta T \ll 1$, $\gamma_B\Delta T \ll 1$

This indicates that where the temperature coefficients of the two materials are sufficiently small, the variation with temperature of the output signal will also be sufficiently small.

Now, the equations (8) and (10) are compared, their difference lies in that the coefficients of $R_1/R_2$ and $R_A/R_B$ are different, for easiness of comparison, we suppose that $R_1/R_2 = R_A/R_B$ and $\gamma_1 = \gamma_A$. To compare the magnitudes of variations with temperature of $V_{T2}'$ and $V_{T2}$, that is to compare which one of $(1+\gamma_1\Delta T)$ and equation (11) more approaching 1, the more one approaches 1, the better the thermo-stability of this element is. It is considered in two situations:

(i) where $\Delta T > 0$

For ordinary ceramic semiconductors, their temperature coefficients are always negative, i.e., $\gamma_A < 0$ and $\gamma_B < 0$, thus we have:

$$0 < 1 + \gamma_A\Delta T < 1 \text{ and } 0 < 1 + \gamma_B\Delta T < 1$$

therefore:

where $|\gamma_A| > |\gamma_B|$, $$\frac{1 + \gamma_A \Delta T}{1 + \gamma_B \Delta T}$$

is more approaching 1 than $1+\gamma_1\Delta T$ (provided that $\gamma_1 = \gamma_A$);

where $|\gamma_A| = |\gamma_B|$, $$\frac{1 + \gamma_A \Delta T}{1 + \gamma_B \Delta T}$$

is more approaching 1 than $1+\gamma_1\Delta T$;

where $|\gamma_A| < |\gamma_B|$, it is indefinite.

(ii) where $\Delta T < 0$, we have:

$$1+\gamma_A\Delta T > 1 \text{ and } 1+\gamma_B\Delta T > 1$$

therefore:

where $|\gamma_A| > |\gamma_B|$, $$\frac{1 + \gamma_A \Delta T}{1 + \gamma_B \Delta T}$$

is more approaching 1 than $1+\gamma_1\Delta T$;

where $|\gamma_A| = |\gamma_B|$, $$\frac{1 + \gamma_A \Delta T}{1 + \gamma_B \Delta T}$$

is more approaching 1 than $1+\gamma_1\Delta T$;

where $|\gamma_A| < |\gamma_B|$, it is indefinite.

In summary, the following conclusion can be obtained: It is only needed to select the gas sensitive materials constituting the two portions of the combined gas sensor to satisfy the following condition:

$\gamma_A$ equals or approximately equals $\gamma_B$, or $|\gamma_A| > |\gamma_B|$, then the thermo-stability of the combined gas sensor is better than that of the gas sensor with common structure. Of course, if the temperature coefficients of both materials are very small, the thermo-stability of the element will also be desirable.

Discussion on the response time and recovery time

1. Response time

Supposing that after the material contacted the gas, its resistance response satisfies $$R' = Re^{-\frac{t}{\tau}}$$

(where $\tau$ is a time constant and R is the resistance in clean air)

then, for the combined gas sensor of the present invention as shown in FIG. 1, for material A:

$$R_A' = R_A e^{-\frac{t}{\tau_A}}$$

where $\tau_A$ is the time constant of material A; and for material B:

$$R_B' = R_B e^{-\frac{t}{\tau_B}}$$

where $\tau_B$ is the time constant of material B.

After the element contacts the gas, its output voltage changes from $V_T$ to $V_T'$, then $$\frac{V_T'}{V_T} = \frac{R_B'/(R_A' + R_B')}{R_B/(R_A + R_B)}$$

$$= \frac{R_B e^{-\frac{t}{\tau_B}}(R_A + R_B)}{R_B(R_A e^{-\frac{t}{\tau_A}} + R_B e^{-\frac{t}{\tau_B}})}$$

$$= \frac{1 + R_B/R_A}{\exp\left(-\frac{t}{\tau_A} + \frac{t}{\tau_B}\right) + R_B/R_A}$$

where $\tau_A = \tau_B$, $V_T' = V_T$;
where $\tau_A < \tau_B$, $V_T' > V_T$, quick response;
where $\tau_A > \tau_B$, $V_T' < V_T$, slow response.

For the gas to be detected, $\tau_A < \tau_B$ is required, i.e., the response of material A is quicker than that of material B; while for interference gas, $\tau_A > \tau_B$ is required, i.e., the response of material A is slower than that of material B.

2. Recovery time

Supposing that the resistance recovery after the material separated from the gas satisfied:

$$R_S = R'(1 - e^{-\frac{t}{\tau}}), \text{ then}$$

the resistance of material A:

$$R_{AS} = R_A'(1 - e^{-\frac{t}{\tau_A}}),$$

and the resistance of material B:

$$R_{BS} = R_B'(1 - e^{-\frac{t}{\tau_B}}),$$

Supposing that the output voltage of the element changes from $V_T'$ to $V_{TS}$, then $$\frac{V_{TS}}{V_T'} = \frac{R_{BS}(R_A' + R_B')}{R_B'(R_{AS} + R_{BS})}$$

$$= \frac{R_B'(1 - e^{-\frac{t}{\tau_B}})(R_A' + R_B')}{R_B'[R_A'(1 - e^{-\frac{t}{\tau_A}}) + R_B'(1 - e^{-\frac{t}{\tau_B}})]}$$

$$= \frac{R_A' + R_B'}{R_A'\zeta + R_B'}$$

where $\zeta = \dfrac{1 - e^{-\frac{t}{\tau_A}}}{1 - e^{-\frac{t}{\tau_B}}}$ where $\zeta = 1$, i.e., $\tau_A = \tau_B$, then $V_{TS} = V_T'$
where $\zeta > 1$, i.e., $\tau_A < \tau_B$, then $V_{TS} < V_T'$, quick recovery;
where $\zeta < 1$, i.e., $\tau_A > \tau_B$, then $V_{TS} > V_T'$, slow recovery.

For the gas to be detected, $\tau_A < \tau_B$ is required, that is, the recovery of material A is quicker than that of material B, this condition is the same as the condition for quick response.

Discussion on initial relaxation time

Normally, there is an initial relaxation time for each of the existing gas sensors, that is, when the heating voltage is turned on, the resistance of the element changes from high to low, which, after a period of time, gradually goes up again and approaches a stable value. The time required from power turn-on to reaching a stable resistance is called the initial relaxation time. The existence of the initial relaxation time causes a lot of troubles. The present invention selects two materials having approximately the same magnitude of initial rising and dropping of resistance and similar relaxation time to constitute the integral combined gas sensor, then the output voltage $V_T$, i.e., the partial voltage of portions A and B, can be maintained stable, thereby, reducing the initial relaxation time of the element, and improving the initial stability of the element.

Discussion on anti-humidity capability

Normally, gas sensors are always affected by humidity, the main cause is that the resistance of an element varies with the humidity. Therefore, changes in humidity will result in the instability of the gas sensor. In order to prevent the interference of humidity variations, besides the conditions mentioned above, the present invention also takes into consideration, in selecting the two gas sensitive materials A and B, to render the variations of resistance with humidity of the two materials A and B as equivalent as possible so as to make the variations of resistance with humidity offset each other by their mutual compensating effect, thereby, the anti-humidity capability of the integral gas sensor can be improved.

DESCRIPTION OF THE EMBODIMENTS

(1) Sintered type

Figure 5:
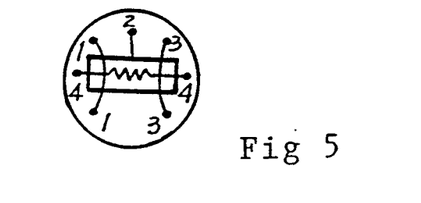
FIG. 5 is a schematic diagram of the sintered gas sensor after potting according to the present invention.

The sectional view of a sintered gas sensor is shown in FIG. 5, it employs a ceramic tube as carrier, and produces three groups of mutually separated electrodes thereon, as indicated by 1, 2, and 3 in FIG. 5, they are produced for grounding, output signal $V_T$ and working voltage $V_C$ respectively. A heating electrode 4 is positioned in the ceramic tube. Gas sensitive material B is coated between electrodes 1 and 2, while gas sensitive material A is coated between electrodes 2 and 3, and after certain sintering processing, the tube core is then welded on the substrate (as shown in FIG. 5), a gas sensor of the present invention is thus obtained after potting.

(2) Thin and thick film type

Figure 6:
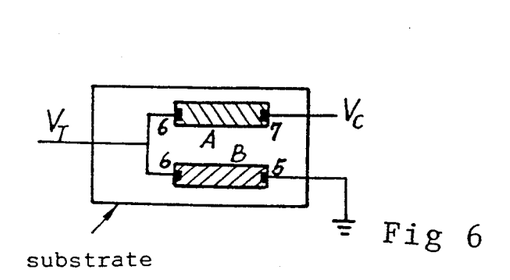
FIG. 6 shows a front schematic diagram of the thin and thick element according to the present invention.

FIG. 6 is a front view of the thin and thick film gas sensor of the present invention.

Figure 7:
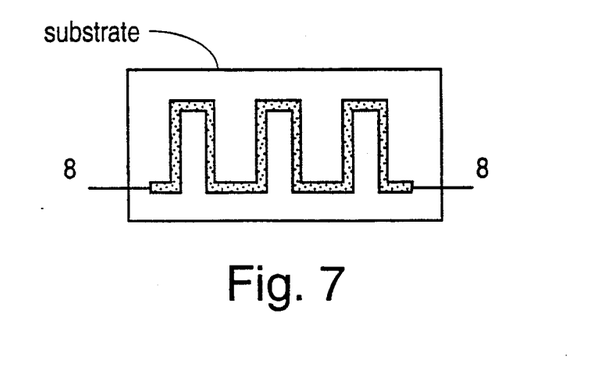
FIG. 7 shows a back schematic diagram of the thin and thick film element according to the present invention.

FIG. 7 is a back view of the thin and thick film gas sensor having its heating electrode produced on the back surface. The three groups of electrodes of a thin and thick film element are produced by mounting $RuO_2$ or Pt on a ceramic substrate, or silicon plate with $SiO_2$ on its surface, or glass substrate, as indicated by 5, 6 and 7 in FIG. 6, they are also produced for grounding, output signal $V_T$ and working voltage $V_C$ respectively. Then, after the processes of evaporation, sputtering and gas-phase deposition (including plasma gas-phase deposition), material A is deposited between electrodes 6 and 7, while material B is deposited between electrodes 5 and 6. If the heating electrode is produced on the front surface, then an insulating layer should coat the heating electrode before the materials A and B being deposited thereon; else if the heating electrode 8 is produced on the back surface (as shown in FIG. 7), it is not necessary to deposit any insulating layer. After completion of the above processes, the tube core is welded on the substrate.

(3) Particular examples

Exploiting the principle of the present invention, a butane sensitive element is manufactured adopting N-N combination. The sensitive body A is made from materials $SnO_2$, $WO_3$, $SiO_2$, $ThO_2$, Pt, porcelain powder, mordanting asbestos with composition ratio of 51.2%, 24%, 10.3%, 10.3%, 0.8%, 1.7%, 1.7% by weight respectively, which are mixed thoroughly and ground sufficiently to produce a paste to coat on a porcelain tube provided with electrodes, and then sintered at a constant temperature of 600° C. for an hour, such that a sensitive body A is produced. The sensitive body B is made from materials $ZnSnO_3$, $SnO_2$, $ThO_2$, $TiO_2$, MgO, $Co_2O_3$, Sb, $Al_2O_3$, mordanting asbestos and porcelain powder with composition ratio of 54.4%–56.7%, 27.5%–29.8%, 1%, 0.5%, 4.7%, 1%, 3.6%, 2%, 1.5%, 15% by weight, which are mixed thoroughly and ground sufficiently to form a paste to coat on the other half of the porcelain tube provided with electrodes, and then sintered at a constant temperature of 600° C. for an hour, such that the sensitive body B is produced. Thereby an integral gas sensor constituted by A and B is produced, which is a butane sensitive element with high selectivity, its results of detections of butane, gasoline, alcohol and acetone are listed in table 1.

It can be seen from the data in Table 1, where the density of butane is 100 ppm, the output voltage value $V_T$ is 1057 mv, which is greater than that of the inferference gases gasoline, alcohol and acetone at 5000 ppm, this indicates that the element is of quite good selectivity.

A butane gas sensor with high selectivity can also be produced with A and B adopting different compositions of sensitive materials and different manufacturing techniques from that mentioned above, the results of testing of the element obtained are listed in Table 2.

Figure 8:
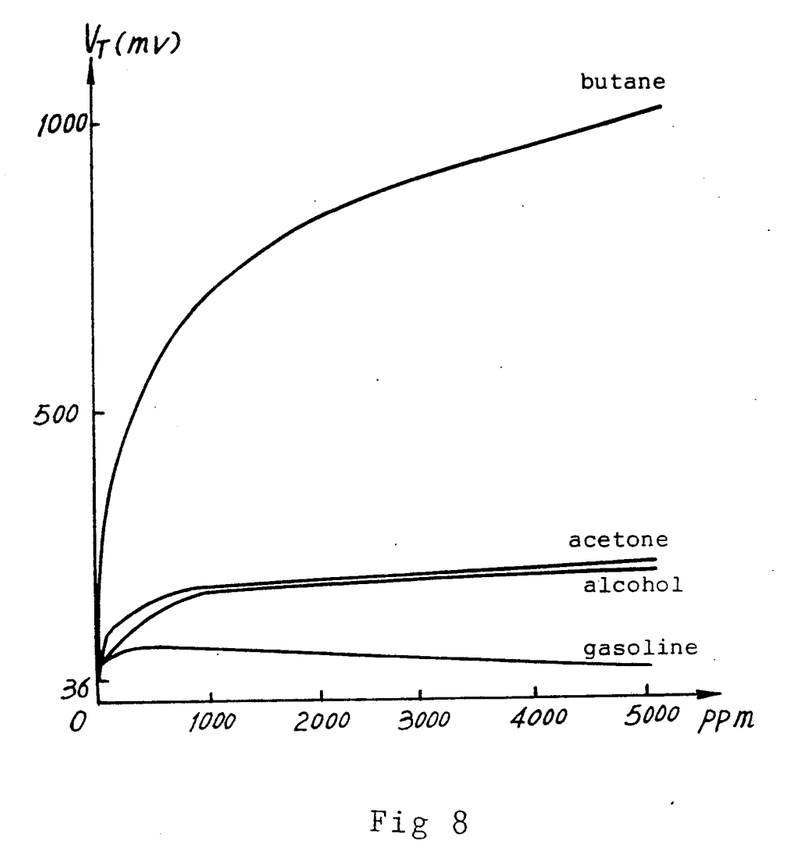
FIG. 8 shows a testing graph of an embodiment of the present invention.

Curves depicted from the data in Table 2 are shown in FIG. 8, these four curves reflect that where the density of the three gases of acetone, alcohol and gasoline exceeds 1000 ppm, the output signal voltages $V_T$ rise very slowly or have the tendency of going down, however, for butane, the output voltage $V_T$ rises as its density increases, thereby, the interference gases can be distinguished effectively from the gas to be detected.

Figure 9:
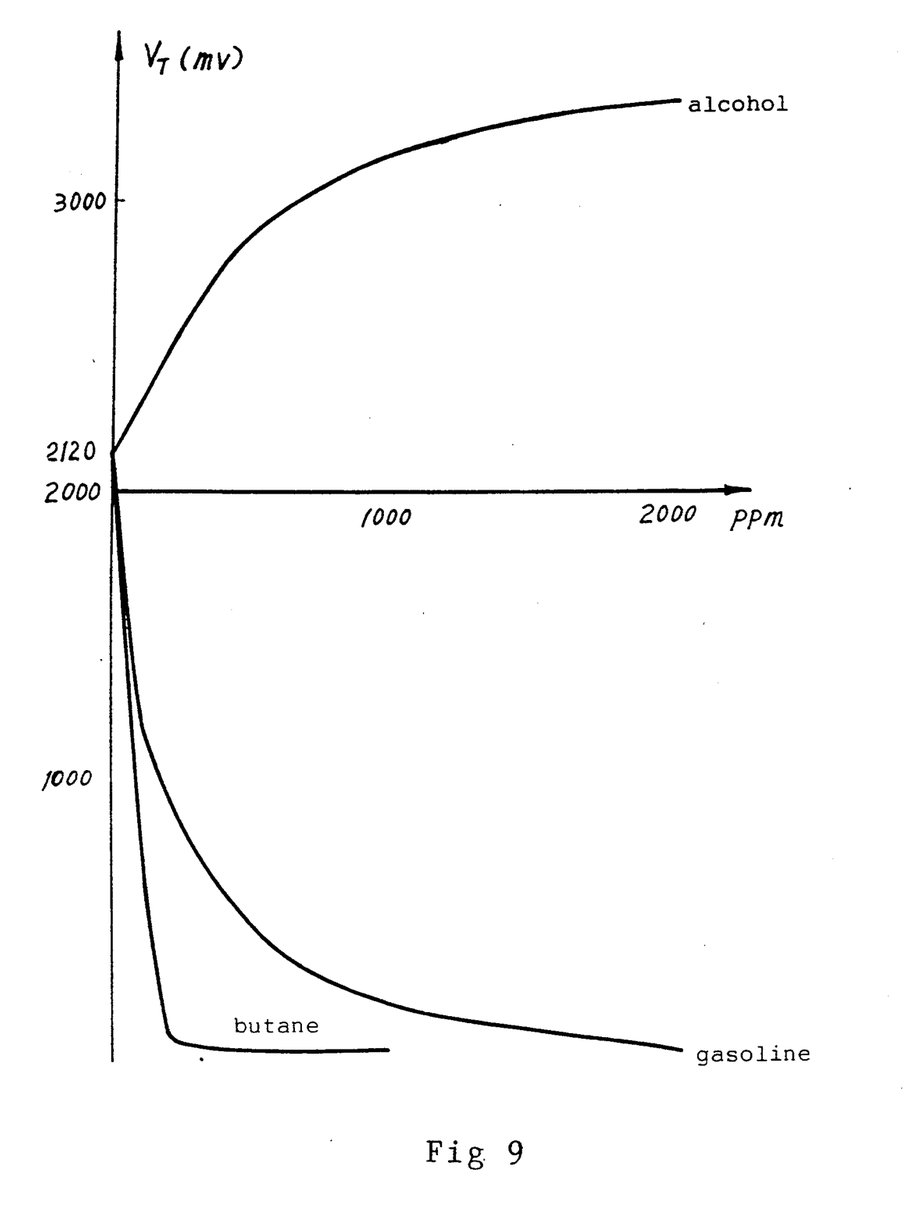
FIG. 9 shows a testing graph of another embodiment of the present invention.

Another embodiment of the present invention illustrates an N-N-type alcohol sensitive element with high selectivity produced by different gas sensitive materials and sintering techniques from the above mentioned embodiments. Wherein, the constituting materials for preparing sensitive body A are: $ZnSnO_3$, $SnO_2$, $Al_2O_3$, CaO, $Ag_2O$, Sb and porcelain powder with composition ratio of 51.4%, 41.1%, 1.5%, 2%, 1.5%, 1% and 1.5% respectively. The materials except Sb and porcelain powder are mixed thoroughly and ground sufficiently first, then the mixture is mixed and stirred to wet with deionized water and pressed into block shape, and heated at constant temperature of 1000° C. for two hours, after cooling naturally, the blocks are pounded and ground, and mixed with Sb and porcelain powder thoroughly, then ground sufficiently, and stirred into paste with deionized water to coat on a porcelain tube provided with electrodes, thereby a sensitive body A is prepared after sintering at a constant temperature of 900° C. for an hour. The materials for sensitive body B are $WO_3$, $Al_2O_3$, and porcelain powder with composition ratio of 90.4%–91%, 3%–3.1% and 6%–6.5%. The materials are mixed thoroughly and ground sufficiently to prepare a paste to coat on the other half of the porcelain tube provided with electrodes, and sintered at a constant temperature of 600° C. for an hour, thereby, a sensitive body B is prepared. An N-N-type alcohol sensor of high selectivity is thus constituted by such two portions A and B. The results of tests on the three gases of alcohol, butane and gasoline are shown in FIG. 9. These three curves reveal that the output voltage $V_T$ increases as the density of alcohol increases, while decreases as the density of butane and gasoline increases. Therefore the selectivity of this gas sensor to alcohol is extremely significant.

The following two embodiments are implemented based on the principle of the present invention by employing $SnO_2$ as substrate material and doping with Pt, $Co_3O_4$, porcelain powder and other materials to prepare sensitive body A and employing $MoO_3$ as substrate material and doping with porcelain powder and other materials to prepare sensitive body B, thereby constituting an N-P-type gas sensor, the results of tests of which on the three gases of alcohol, gasoline and butane are listed in Table 3.

It can be learnt from table 3 that both sensitivities $\beta$ of the two N-P-type gas sensors in table 3 are higher than the sensitivity $\beta_1$ or $\beta_2$ of each of the gas sensitive materials constituting the integral gas sensor.

The scope sought to be protected by the present application for a patent for invention is defined by the attached claims.

TABLE 1

| | $V_C = 10V, V_H = 5V$ | | | | | |
|---|---|---|---|---|---|---|
| | Density of Gas | | | | | |
| Gas Tested | 0 (ppm) | 100 (ppm) | 500 (ppm) | 1000 (ppm) | 2000 (ppm) | 5000 (ppm) |
| | | | output voltage | | | |
| Butane | 169 | 1057 | 1190 | 1143 | 1129 | 1042 |
| Gasoline | 149 | 314 | 412 | 381 | 336 | 270 |
| Alcohol | 188 | 127 | 150 | 190 | 261 | 237 |
| Acetone | 142 | 466 | 648 | 750 | 820 | 850 |

TABLE 2

| | $V_C = 10V, V_H = 5V$ | | | | | |
|---|---|---|---|---|---|---|
| | Density of Gas | | | | | |
| Gas Tested | 0 (ppm) | 100 (ppm) | 500 (ppm) | 1000 (ppm) | 2000 (ppm) | 5000 (ppm) |
| | | | output voltage | | | |
| Butane | 36 | 306 | 550 | 690 | 830 | 1015 |
| Gasoline | 36 | 75 | 100 | 92 | 81 | 65 |
| Alcohol | 36 | 83 | 147 | 192 | 199 | 218 |
| Acetone | 36 | 118 | 164 | 190 | 213 | 215 |

TABLE 3

| | | $V_C = 10V, V_H = 5V$ | | | | | | | | |
|---|---|---|---|---|---|---|---|---|---|---|
| | | gas to be tested | | | | | | | | |
| No. | | Alcohol | | | gasoline | | | butane | | |
| of | density | | | | sensitivity | | | | | |
| element | (ppm) | $\beta$ | $\beta_1$ | $\beta_2$ | $\beta$ | $\beta_1$ | $\beta_2$ | $\beta$ | $\beta_1$ | $\beta_2$ |
| I | 100 | 35 | 13 | 1.64 | 14 | 4.5 | 1.6 | | | |
| | 500 | 158 | 77 | 2.3 | 45 | 45 | 1.9 | | | |
| | 1000 | 218 | 142 | 2.6 | 98 | 33 | 2.3 | 37 | 10 | 1.5 |
| | 2000 | | | | | | | 50 | 25 | 1.6 |
| II | 100 | 56 | 13 | 2.03 | 11 | 4.6 | 1.4 | | | |
| | 500 | 219 | 78 | 3.06 | 29 | 11 | 1.7 | | | |
| | 1000 | 307 | 170 | 3.51 | 51 | 20 | 1.9 | 20 | 10 | 1.2 |
| | 2000 | | | | | | | 32 | 15 | 1.3 |

What is claimed is:

1. A combined semiconductor gas sensor for measuring the density of a specific gas, comprising the combination of two portions, which portions are formed on a single substrate and are made of two different gas sensitive materials respectively, wherein the resistances of these two portions vary differently with the density of the specific gas; when said gas sensor is coupled into a detecting circuit, an output signal is led out from the junction of said two portions, wherein one of the portions serves as the load simultaneously, an absolute value of the temperature coefficient of the gas sensitive material constituting the portion serving as the load simultaneously is not greater than an absolute value of the temperature coefficient of the material constituting the other portion.

2. The gas sensor according to claim 1, wherein the temperature coefficients of said two portions are equal to or approximately equal to each other.

3. The gas sensor according to claim 1, wherein both gas sensitive materials are N-type, the combined gas sensor being of N-N-type, wherein one gas sensitive material is sensitive to the gas to be detected but insensitive to interference gas(es), while the other gas sensitive material is sensitive to interference gas(es) but insensitive to the gas to be detected.

4. The gas sensor according to claim 1, wherein one material is N-type, and the other is P-type respectively, and both of them are sensitive to the gas to be detected.

5. The gas sensor according to claim 4, wherein both gas sensitive materials are insensitive to interference gases.

6. The gas sensor according to claim 1, wherein the gas sensor is of sintered type.

7. The gas sensor according to claim 3, wherein the portion serving as load is made from the following materials:
   $ZnSnO_3$, 54.4%–56.7% by weight,
   $SnO_2$, 27.5%–29.8% by weight,
   $ThO_2$, 1% by weight,
   $TiO_2$, 0.5% by weight,
   MgO, 4.7% by weight,
   $Co_2O_3$, 1% by weight,
   Sb, 3.6% by weight,
   $Al_2O_3$, 2% by weight,
   mordanting asbestos, 1.5% by weight, and
   porcelain powder, 1.5% by weight;
and the other portion is made from:
   $SnO_2$, 51.2% by weight,
   $WO_3$, 24% by weight,
   $SiO_2$, 10.3% by weight,
   $ThO_2$, 10.3% by weight,
   Pt, 0.8% by weight,
   porcelain powder, 1.7% by weight, and
   mordanting asbestos, 1.7% by weight.

8. The gas sensor according to claim 3, wherein the portion serving as load is made from the following materials:
   $WO_3$, 90.4%–91% by weight,
   $Al_2O_3$, 3%–3.1% by weight, and
   porcelain powder, 6%–6.5% by weight;
and the other portion is made from:
   $ZnSnO_3$, 51.4% by weight,
   $SnO_2$, 41.1% by weight,
   $Al_2O_3$, 1.5% by weight,
   CaO, 2% by weight,
   $Ag_2O$, 1.5% by weight,
   Sb, 1% by weight, and
   porcelain powder, 1.5% by weight.

9. The gas sensor according to claim 1, wherein both gas sensitive materials are P-type, the combined gas sensor being of P-P-type, wherein one gas sensitive material is sensitive to the gas to be detected but insensitive to interference gas(es), while the other gas sensitive material is sensitive to interference gas(es) but insensitive to the gas to be detected.

10. The gas sensor according to claim 4, wherein both gas sensitive materials are insensitive to interference gases.

11. The gas sensor according to claim 1, wherein the gas sensor is of thin film type.

12. The gas sensor according to claim 1, wherein the gas sensor is of thick film type.

13. A combined gas sensor for measuring the density of a specific gas, the gas sensor comprising:
   a first portion of a gas sensitive material, the first portion having a first end and a second end, such that when the first portion is exposed to the specific gas, the resistance between the first and second ends across the first portion varies with the density of the specific gas;

a second portion of a gas sensitive material, the second portion having a first end and a second end, such that when the second portion is exposed to the specific gas, the resistance between the first and second ends of the second portion across the second portion varies with the density of the specific gas differently from said resistance across the first portion;

a first electrode connected to the first end of the first portion;

a second electrode connected to the second end of the second portion, the first and second electrodes being for passing a current therebetween through the first and second portions; and a third electrode connected to the second end of the first portion and the first end of the second portion, for providing an output signal indicative of the density of the specific gas.

14. The combined gas sensor of claim 13 wherein the first and second portions are formed on a single substrate.

15. The combined gas sensor of claim 14 wherein the substrate is a ceramic tube.

16. The combined gas sensor of claim 13 wherein the output signal is a voltage determined by the ratio of said resistance across the first portion to said resistance across the second portion.

17. The combined gas sensor of claim 13 wherein the first portion has a greater sensitivity to the specific gas than the second portion, and the first portion has a smaller sensitivity to an interference gas than the second portion.

18. The combined gas sensor of claim 13 whose sensitivity to the specific gas is greater than a sensitivity to the specific gas of the first portion and greater than a sensitivity to the specific gas of the second portion.

19. The combined gas sensor of claim 13 whose resolution to the specific gas and an interference gas is greater than a resolution to the specific gas and the interference gas of the first portion and greater than a resolution to the specific gas and the interference gas of the second portion.

20. The combined gas sensor of claim 13 wherein variations of said resistance across the first and second portions with humidity at least partially offset each other to reduce variation of the output signal with humidity.

21. The gas sensor of claim 13, further comprising means for connecting the first electrode to a first voltage and the second electrode to a second voltage lower in magnitude than the first voltage, wherein, for the specific gas, a time constant of the resistance response of the first portion is smaller than a time constant of the resistance response of the second portion.

22. The gas sensor of claim 13, further comprising means for connecting the first electrode to a first voltage and the second electrode to a second voltage lower in magnitude than the first voltage, wherein, for an interference gas, a time constant of the resistance response of the first portion is greater than a time constant of the resistance response of the second portion.

23. The combined gas sensor of claim 13 wherein:

for the specific gas, a time constant of the resistance response of the first portion is smaller than a time constant of the resistance response of the second portion, and for an interference gas, a time constant of the resistance response of the first portion is greater than a time constant of the resistance response of the second portion.

24. The combined gas sensor of claim 13 wherein an initial relaxation time of the first portion is equal or approximately equal to an initial relaxation time of the second portion.

* * * * *